(12) United States Patent
Petersen

(10) Patent No.: US 8,216,561 B2
(45) Date of Patent: Jul. 10, 2012

(54) POLYACRYLAMIDE HYDROGEL FOR THE TREATMENT OF INCONTINENCE AND VESICOURETAL REFLEX

(75) Inventor: Jens Petersen, Birkerød (DK)

(73) Assignee: Contura A/S, Soborg (DK)

(*) Notice: Subject to any disclaimer, the term of this patent is extended or adjusted under 35 U.S.C. 154(b) by 1592 days.

(21) Appl. No.: 11/469,213

(22) Filed: Aug. 31, 2006

(65) Prior Publication Data

US 2007/0020226 A1 Jan. 25, 2007

Related U.S. Application Data

(62) Division of application No. 09/938,667, filed on Aug. 27, 2001, now Pat. No. 7,780,958.

(60) Provisional application No. 60/228,081, filed on Aug. 25, 2000.

(51) Int. Cl.
*A61K 31/74* (2006.01)
*A61K 31/785* (2006.01)
*A61K 31/765* (2006.01)
*A61F 13/00* (2006.01)
*A61F 2/00* (2006.01)

(52) U.S. Cl. .............. 424/78.31; 424/78.35; 424/78.27; 424/78.33; 424/422; 424/423

(58) Field of Classification Search ............... 424/78.27, 424/78.31, 78.35, 422, 423
See application file for complete search history.

(56) References Cited

U.S. PATENT DOCUMENTS

| | | | |
|---|---|---|---|
| 3,867,329 A | 2/1975 | Halpern et al. | |
| 3,948,862 A | 4/1976 | Iwasyk | |
| 4,074,039 A | 2/1978 | Lim et al. | |
| 4,344,193 A | 8/1982 | Kenny | |
| 4,502,161 A | 3/1985 | Wall | |
| 4,535,131 A | 8/1985 | Handa et al. | |
| 4,540,568 A | 9/1985 | Trager et al. | |
| 4,540,569 A | 9/1985 | Ohnishi et al. | |
| 4,571,749 A | 2/1986 | Fischell | |
| 4,657,656 A | 4/1987 | Ogawa | |
| 4,713,434 A | 12/1987 | Sutterlin et al. | |
| 4,746,551 A | 5/1988 | Allen et al. | |
| 4,857,041 A | 8/1989 | Annis et al. | |
| 4,919,667 A | 4/1990 | Richmond | |
| 4,969,474 A | 11/1990 | Schwarz | |
| 5,135,480 A | 8/1992 | Bannon et al. | |
| 5,171,322 A | 12/1992 | Kenny | |
| 5,244,799 A | 9/1993 | Anderson | |
| 5,306,404 A | 4/1994 | Notsu et al. | |
| 5,344,451 A | 9/1994 | Dayton | |
| 5,344,459 A | 9/1994 | Swartz | |
| 5,482,719 A | 1/1996 | Guillet et al. | |
| 5,516,532 A | 5/1996 | Atala et al. | |
| 5,589,104 A | 12/1996 | Bambeck | |
| 5,652,274 A | 7/1997 | Martin | |
| 5,658,329 A | 8/1997 | Purkait | |
| 5,667,778 A | 9/1997 | Atala | |
| 5,700,289 A | 12/1997 | Breitbart et al. | |
| 5,709,854 A | 1/1998 | Griffith-Cima et al. | |
| 5,798,096 A | 8/1998 | Pavlyk | |
| 5,813,411 A | 9/1998 | Van Bladel et al. | |
| 5,854,382 A | 12/1998 | Loomis | |
| 5,902,832 A | 5/1999 | Van Bladel et al. | |
| 5,941,909 A | 8/1999 | Purkait | |
| 6,005,020 A | 12/1999 | Loomis | |
| 6,060,053 A | 5/2000 | Atala | |
| 6,129,761 A | 10/2000 | Hubbell | |
| 6,252,016 B1 | 6/2001 | Wu et al. | |
| 6,277,948 B1 | 8/2001 | Zahr | |
| 6,335,028 B1 | 1/2002 | Vogel et al. | |
| 6,486,213 B1 | 11/2002 | Chen et al. | |
| 6,544,503 B1 | 4/2003 | Vanderhoff et al. | |
| 6,592,859 B1 | 7/2003 | Bley | |
| RE38,913 E | 12/2005 | Pavlyk | |
| 7,186,419 B2 * | 3/2007 | Petersen | 424/423 |
| 7,678,146 B2 * | 3/2010 | Petersen et al. | 623/11.11 |
| 7,780,958 B2 * | 8/2010 | Petersen | 424/78.35 |
| 7,790,194 B2 * | 9/2010 | Petersen | 424/423 |
| 2002/0064512 A1 | 5/2002 | Petersen et al. | |
| 2002/0150550 A1 | 10/2002 | Petersen | |
| 2002/0187172 A1 | 12/2002 | Reb et al. | |
| 2003/0065389 A1 | 4/2003 | Petersen | |
| 2003/0077244 A1 | 4/2003 | Petersen | |
| 2003/0171509 A1 | 9/2003 | Balestrieri et al. | |
| 2003/0176602 A1 | 9/2003 | Schmidt et al. | |
| 2005/0175704 A1 | 8/2005 | Petersen | |

FOREIGN PATENT DOCUMENTS

| | | |
|---|---|---|
| CN | 1228447 | 9/1999 |
| EP | 0153672 A2 | 9/1985 |
| EP | 0 248 544 | 12/1987 |
| EP | 0153672 B1 | 5/1989 |
| EP | 0496067 A2 | 7/1992 |
| EP | 0555119 A1 | 8/1993 |
| EP | 0727232 A2 | 8/1996 |
| EP | 0 730 847 | 9/1996 |
| EP | 0727232 A3 | 11/1996 |

(Continued)

OTHER PUBLICATIONS

U.S. Appl. No. 11/469,213, filed Aug. 31, 2006, Petersen.
J.E. Gomez and G.B. Thurston, Comparisons of the oscillatory shear viscoelasticity and composition of pathological synovial fluids, Biorheology 30, 409-427 (1993).
Gale Encyclopedia of Medicine, Dec. 2002, under Urinary incontinence.
Lise Christensen M.D. Ph.D. et al, "Adverse Reactions to Injectable Soft Tissue Permanent Fillers", Aesthetic Plastic Surgery 29:34-48, 2005.
Gebauer et al., Gonarthritis due to *Salmonella enteritidis* in a patient with systemic lupus erythematosus, Klinische Padiatrie, (Sep.-Oct. 2002) 214 (5), 319-323, Abstract.

(Continued)

Primary Examiner — Blessing Fubara
(74) Attorney, Agent, or Firm — Hunton & Williams LLP

(57) ABSTRACT

The present invention relates to a bio-stable hydrogel for use in the treatment and prevention of incontinence and vesicouretal reflux. The hydrogel is obtainable by combining acrylamide and methylene bis-acrylamide in amounts to provide about 0.5 to 25% by weight polyacrylamide, based on the total weight of the hydrogel.

32 Claims, No Drawings

FOREIGN PATENT DOCUMENTS

| | | |
|---|---|---|
| EP | 0742022 A1 | 11/1996 |
| EP | 0 774 981 | 5/1997 |
| EP | 0 826 381 | 3/1998 |
| EP | 0 830 416 | 3/1998 |
| EP | 0 895 785 | 2/1999 |
| EP | 1 059 943 | 12/2000 |
| EP | 1 274 472 | 1/2003 |
| GB | 1317408 | 5/1973 |
| GB | 1320233 | 6/1973 |
| GB | 2114578 | 6/1980 |
| GB | 2114578 | 8/1983 |
| RU | 1831709 | 7/1993 |
| RU | 2034465 | 5/1995 |
| RU | 2148957 | 2/1998 |
| RU | 2127129 | 3/1999 |
| RU | 2148957 | 5/2000 |
| SU | 1608193 | 11/1990 |
| SU | 1687291 | 10/1991 |
| SU | 1697756 A1 | 12/1991 |
| WO | WO 81/01290 | 5/1981 |
| WO | WO 89/07455 | 8/1989 |
| WO | WO 93/19702 | 10/1993 |
| WO | WO 96/04026 | 2/1996 |
| WO | WO 96/04943 | 2/1996 |
| WO | WO 96/25129 | 8/1996 |
| WO | WO 96/39464 | 12/1996 |
| WO | WO 98/25575 | 6/1998 |
| WO | WO 99/10021 | 3/1999 |
| WO | WO 99/15211 | 4/1999 |
| WO | WO 99/44643 | 9/1999 |
| WO | WO 00/31148 | 6/2000 |
| WO | WO 00/59411 | 10/2000 |
| WO | WO 00/78356 | 12/2000 |
| WO | WO 01/32129 | 5/2001 |
| WO | WO 01/38402 | 5/2001 |
| WO | WO 01/42312 A1 | 6/2001 |
| WO | WO 01/47431 | 7/2001 |
| WO | WO 01/47433 | 7/2001 |
| WO | WO 01/49336 A1 | 7/2001 |
| WO | WO 01/50833 | 7/2001 |
| WO | WO 01/70289 | 9/2001 |

OTHER PUBLICATIONS

Jarosova et al., Analysis of clinical and laboratory data in a group of patients with juvenile idiopathic arthritis (JIA) in the framework of the national register, Ceska Revmatologie, (2002) 10/2 (65-70), Abstract.

N.A. Peppas, 1986, *Hydrogels in Medicine and Pharmacy*.

Int'l Search Report dated Jan. 31, 2002 for Int'l. Appl. No. PCT/DK01/00565 Filed Aug. 25, 2001.

Russian Federation, Irkutsk Region, Regional Licensing-Accreditation Commission, License Registration No. 94, (May 20, 1994) (Abstract).

Ministry of Public Health of Ukraine, Kiev Research Institute of Hematology and Blood Transfusion, Report dated Feb. 29, 1993.

Interfall's Biocompatible Hydrogel, Doctor's Information (Feb. 22, 2006) (citing U.S. Patent. No. 5,798,096) at http://www.bpg.bg/interfall/EB005140106biocompatible_gel1.htm.

Stevens, Malcolm P., Definitions, "Polymer Chemistry: An Introduction", Third Edition, Oxford University Press, Inc., Sect. 1.2, pp. 6-10, 1999.

Lewis, Richard J., Sr., Olefin (alkene), "Hawley's Condensed Chemical Dictionary", Thirteenth Edition, John Wiley & Sons, Inc., p. 819, 1997.

O'neil, Maryadele J., et al. (Eds.), Acrylamide, "The Merck Index: An Encyclopedia of Chemicals, Drugs, and Biologicals", Thirteenth Edition, Merck Research Laboratories, Merck & Co., Inc., Listing No. 131, p. 128, 2001.

\* cited by examiner

POLYACRYLAMIDE HYDROGEL FOR THE TREATMENT OF INCONTINENCE AND VESICOURETAL REFLEX

REFERENCE TO PRIOR APPLICATION

This application is a divisional of U.S. application Ser. No. 09/938,667, filed Aug. 27, 2001, now U.S. Pat. No. 7,780,958 which claims priority under 35 U.S.C. §119(e) from provisional application Ser. No. 60/228,081, filed Aug. 25, 2000.

FIELD OF THE INVENTION

Polyacrylamide hydrogels are used herein as endoprosthetic devices for bulking the urethra, rectum or colon (or canalis analis) or ureter in order to increase resistance in these conduits for the treatment of urinary incontinence, anal incontinence, and vesicouretal reflux. The polyacrylamide hydrogels comprises 0.5 to 25% by weight polyacrylamide and either pyrogen-free water or saline solution.

BACKGROUND OF THE INVENTION

The loss of voluntary control of sphincter muscles underlies urinary and anal incontinence. Urinary incontinence, the inability to voluntarily retain one's urine in one's bladder, is common among the elderly. Contraction of the detrusor muscle of the bladder may be voluntary, brought about stress, reflex or urge. Contraction of the detrusor muscle brought about by a stress results in involuntary urination unless the bladder sphincter muscle is voluntarily contracted. In the event that one has lost control of the bladder sphincter muscle, urination may be brought about by slight stress such as slight abdominal contractions during daily activities, sneezing. coughing, laughing, gas retention, surprises and countless other stimuli which may lead to contraction of the detrusor muscle. A similar principle underlies anal incontinence wherein one has diminished control of the anal sphincter muscle. Urinary and anal incontinence may be brought upon by ageing, trauma (such as in paraplegics), or congenitally related.

Vesicouretal reflux is the result of decreased ureteral resistance wherein urine from the bladder refluxes back into the kidney. This can result in the transport of bacteria form the bladder back up through the ureter, clayceal dilation, the renal pyramids and the kidneys and may lead to infections and recurrent pyelonephritis as well as cause physiological injury to the renal parenchyma. This may lead to renal failure.

Urinary incontinence, anal incontinence and vesicouretal reflux may be treated by increasing the resistance of passage through the urethra, the colon or rectum (or canalis analis), and the ureter, respectively, known as bulking processes Attempts to treat urinary incontinence have involved hydraulic apparatuses, such as in WO 01/50833 and U.S. Pat. No. 4,969,474 and other controllable apparatuses such as prosthetic sphincters with inflatable cuffs as in U.S. Pat. No. 4,571,749 and WO 01/47433. Weight loss, exercise, medication and surgical operation usually involving the elevation of the bladder neck or constructing a increasing resistance through the urethra using the surrounding tissue or using a prosthetic material. Materials such as collagen, PTFE, silicone, and Teflon have been used to this end (references to be added).

Anal incontinence has also been addressed via controllable and operated devices such as in WO 01/47431. Vesicouretal reflux has been dealt with surgically (to extend the ureter, usually in the infant) and with antibiotics.

A principle object of the present invention is to provide a polyacrylamide hydrogel to increase the resistance in the relevant conduits in the treatment of incontinence and vesicouretal reflux.

U.S. Pat. No. 6,129,761 discloses the use of injectable hydrogel and cellular compositions towards this end. The compositions are cell suspensions comprising cells mixed with a biocompatible and biodegradable polymer. The polymer provides a medium and template for cell growth and cellular engraftment to the surrounding tissue. Cell growth coincides with polymer degradation to result in the desired tissue growth. The polymeric materials disclosed by U.S. Pat. No. 6,129,761 consist of alginates such as modified alginates. bacterial polysaccharides such as gellan gum, plant polysaccharides such as carrageenans, hyaluronic acids, polyethylene oxide-polypropylene glycol block copolymers, proteins such as fibrin, collagen, and gelatin, mixtures of polyethylene oxide and polyacrylic acid, cross-linked chitosan, photochemically cross-linked ethylenically unsaturated groups, macromers such as PEG-oligolactyl-acrylates, polyethylenimine, poly-lysine, poly(vinylamine), and poly(allylamine). U.S. Pat. No. 6,129,761 does not disclose the use of stable polyacrylamide hydrogels but rather degradable poly(vinylamine). Given the requirement of the polymer of the invention of U.S. Pat. No. 6,129,761 to degenerate according to the method of he invention, biostable polymers, such as the biostable polyacrylamide of the present invention is not suitable for the method of U.S. Pat. No. 6,129,761.

RU2148957 relates to a method for treating cases of vesicoureteral reflux using polyacrylamide hydrogel.

The substances for injection used thus far used are synthetic substances (teflon, silicone, coal particles) and natural substances (connective tissue extract, fat). The long-term effect has been relatively poor with relapses of incontinence among approximately half the treatments after one year of observation. Thus, there is a need to find a substance which is biocompatible with tissue but at the same time is not absorbed or excreted by the body (biostable). Moreover, the substance must have adequate rheological properties to act effectively.

An object of the present invention is to provide a biocompatible and bio-stable polyacrylamide hydrogel for increasing the resistance of conduits for the treatment of incontinence and vesicouretal reflux.

SUMMARY OF THE INVENTION

A first aspect of the invention relates to a bio-stable hydrogel for use in the in the treatment and prevention of incontinence and vesicouretal reflux, said hydrogel obtainable by combining acrylamide and methylene bis-acrylamide in amounts so as to give about 0.5 to 25% by weight polyacrylamide, based on the total weight of the hydrogel; radical initiation; and washing with pyrogen-free water or saline solution.

A further aspect of the invention relates to the use of a bio-stable hydrogel comprising about 0.5 to 25% by weight polyacrylamide, based on the total weight of the hydrogel, for the preparation of an endoprosthesis for the treatment and prevention of incontinence and vesicouretal reflux and to a method of treating or preventing incontinence or vesicouretal reflux comprising administering a hydrogel to a mammal said hydrogel comprising 0.5 to 25% by weight polyacrylamide, based on the total weight of the hydrogel.

An important object of the invention is to provide a prosthetic device for increasing the resistance of conduits selected from the group consisting of the urethra; the rectum or colon; and the ureter for the treatment of urinary incontinence, anal incontinence, and vesicouretal reflux, respectively: wherein said device is injectable and comprising the bio-stable hydrogel of the invention.

GENERAL DESCRIPTION OF THE INVENTION

The term "bio-stable" is intended to mean that the substance does not degrade to any substantial degree in interstitial fluid or body tissue.

A first aspect of the invention relates to the bio-stable hydrogel obtainable by combining acrylamide and methylene bis-acrylamide in amounts so as to give about 0.5 to 25% by weight polyacrylamide, based on the total weight of the hydrogel; radical initiation; and washing with pyrogen-free water or saline solution, for use in the in the treatment and prevention of incontinence and vesicouretal reflux. The bio-stable hydrogel typically has a molecular weight between $0.01\times10^6$ and $20\times10^6$. The polymer is resistant to biological degradation and is not permeable through biological membranes. The polyacrylamide hydrogel of the invention is fully biocompatible (according to ISO standard test ISO-10993). The polyacrylamide hydrogel does not have cytotoxic effect on human fibroblasts, is non-toxic, non-carcinogenic, non-allergenic. non-mutagenic. and resistant to enzymatic and microbiological degradation. Furthermore, the polymer is not water-soluble. The present investigators have found that the bio-stable gel is effective as a bulking agent and suitable for the treatment of incontinence and vesicouretal reflux given the gel is biocompatible, non-biodegradable and does not migrate from the site of application in the conduit.

The bio-stable hydrogel of the invention is typically obtained by combining acrylamide and methylene bis-acrylamide in a molar ratio of 150:1 to 1000:1. In a preferred embodiment, the hydrogel comprises less than 15% by weight polyacrylamide, based on the total weight of the hydrogel, preferably less 10%, more preferably less than 7.5%, even more preferably less than 5%, most preferably less than 3.5% by weight polyacrylamide, based on the total weight of the hydrogel.

Given the hydrogel of the invention is directed for use as a permanent endoprosthesis, it must be stable. Furthermore. given the hydrogel of the invention is directed for use as an endoprosthesis for selected parts of the human anatomy, the hydrogel typically comprises at least 0.5% by weight polyacrylamide, based on the total weight of the hydrogel, preferably at least 1.0% by weight polyacrylamide, more preferable at least 1.5% by weight polyacrylamide, such as at least 1.6% by weight polyacrylamide, based on the total weight of the hydrogel. Typically, the hydrogel of the present invention may have a solid weight content of 1.5, 1.6, 1.7 1.8, 1.9, 2.0, 2.1, 2.2, 2.3, 2.4, 2.5, 2.6, 2.7, 2.8, 2.9, 3.0, 3.1, 3.2, 3.3, 3.4, or 3.5% polyacrylamide, based on the total weight of the hydrogel. For the treatment of vesicouretal reflux, the hydrogel preferably comprises less than 3.5% by weight polyacrylamide, based on the total weight of the hydrogel and about 96.5% pyrogen-free water of saline solution, such as 97.5% pyrogen-free water of saline solution.

The viscosity of the bio-stable hydrogel is typically such that it may be injected. In a suitable embodiment, the hydrogel has a complex viscosity module of about 2 to 50 Pas, such as about 2 to 40 Pas, preferably about 2 to 30 Pas, more preferably about 2 to 20 Pas.

The device may have a viscosity such that it may be injected. In an embodiment wherein the hydrogel is injected, the hydrogel has a complex viscosity module of about 2 to 30 Pa s, such as about 2 to 20 Pa s. preferably about 3 to 18 Pa s, most preferably about 3 to 15 Pa s, such as 3, 4, 5, 6, 7, 8, 9, 10, 11, 12, 13, 14, and 15 Pa s.

The device also has elastic properties due to, at lest in part of the high water binding capacity of the hydrogel of water. This is of great relevance in terms, at least, of durability and ability to provide resistance through the conduit. In a preferred embodiment, the hydrogel of the invention has an elasticity modulus of about 1 to 200 Pa, such as about 2 to 175 Pa, typically about 5 to 150 Pa, such as 10 to 100 Pa.

The elasticity modulus of the prosthetic device and the complex viscosity are typically related by a factor of 5.8 to 6.4. The present invention thus provides for a hydrogel with the advantageous combined features of a viscosity suitable for being injectable and of an elasticity to provide for increase resistance. In a combination of preferred embodiments, the hydrogel has a complex viscosity less than 25 Pa s and an elasticity modulus less than 200 Pa, preferably having a complex viscosity less than 15 Pa s and an elasticity less than 100.

Example 1, Tables 1, 2, 3 and 4 illustrate appropriate conditions for preparing the illustrative examples of hydrogels. As can be seen, within the preferred combined embodiment of a viscosity of less than 25 Pa s and an elasticity modulus of less than 200 Pa, the hydrogel may have an array of dry-weight content percentages.

Furthermore, still within the preferred combined embodiment of a viscosity of less than 25 Pa s and an elasticity less than 200 Pa, such as having a complex viscosity less than 15 Pa s and an elasticity less than 100, the hydrogel is obtainable by combining acrylamide and methylene-bis-acrylamide in a molar ratio of about 275 to 1000, typically 300 to 800, preferably in a ratio of about 300 to 500.

The hydrogel of the invention is substantially free of materials which contribute to the solid weight content other than the acrylamide, methylene-bis-acrylamide and residual amounts (if any) of the initiators. The hydrogel is substantially free of any other polymeric content. The hydrogel further comprises at least 75% by weight pyrogen-free water or saline solution, preferably pyrogen-free water. In a suitable embodiment of the invention, the hydrogel comprises at least 80% by weight pyrogen-free water or saline solution, preferably at least 85%, more preferably at least 90%, even more preferably at least 95% by weight pyrogen-free water or saline solution.

A suitable saline solution has an osmolarity similar to that of interstitial fluid. Suitable saline solutions include but are not limited to the group selected from 0.25-1% aqueous sodium chloride, a Ringer-Lockart solution, an Earle solution, a Hanks solution, an Eagle medium, a 0.25-1% glucose solution, a potassium chloride solution, and a calcium chloride solution. In a preferred embodiment, the saline solution is an about 0.8-1% aqueous sodium chloride solution, such as a 0.8, 0.9 or 1% aqueous sodium chloride solution.

In a particularly suitable embodiment of the invention, the hydrogel comprises about 2.5% by weight polyacrylamide, based on the total weight of the hydrogel and about 97.5% pyrogen-free water.

Pyrogen-free water or saline solution is used for the washing process. The washing process serves, in part, to remove all but trace amounts of the monomers acrylamide and N,N'-methylene-bis-acrylamide. These monomers are toxic to the patient as well as detrimental to the stability of the hydrogel. The washing process is preferably such that the concentrations of the monomers acrylamide and N,N'-methylene-bis-acrylamide are below 50 ppm, more preferably below 40 ppm, such as below 30 ppm, most preferably below 20 ppm, typically below 10 ppm, typically below 5 ppm.

The washing process may suitably be performed for 15 to 250 hours. such as for 20 to 225 hours. From Table 2 and 3, it can be seen that the washing process is typically performed for 50 to 100 hours, more typically for 70 to 100 hours.

In a further embodiment of the invention, the device prosthetic device comprises cells, such as stem cells. Polyacrylamide provides an excellent template and matrix for cell growth. The use of cells with the hydrogel of the invention for the preparation of the device would allow for cellular engraftment to the surrounding tissue in the ureter, urethra or analis Canalis. A device comprising the hydrogel of the invention and the appropriate cells allows for greater resistance and greater efficiency in providing resistance.

In a preferred embodiment, the hydrogel of the invention is for use in the treatment of urinary and anal incontinence, more preferably urinary incontinence.

Urinary incontinence may be stress or reflex urinary incontinence or urge urinary incontinence. Typically, the hydrogel of the invention is suitable for the treatment of stress or reflex urinary incontinence.

In a further aspect of the invention, the present hydrogel is used in the preparation of an endoprosthesis. Thus, a further object of the invention is the use of a hydrogel, as described supra, comprising about 0.5 to 25% by weight polyacrylamide, based on the total weight of the hydrogel, for the preparation of an endoprosthesis for the treatment and prevention of incontinence and vesicouretal reflux.

The endoprosthesis is suitably formulated as an injectable suspension. The suspension comprises a homogenised formulation of the hydrogel. Typically, a syringe is filled with the suspension.

A further object of the invention relates to a method of treating or preventing incontinence or vesicouretal reflux comprising administering a hydrogel to a mammal said hydrogel comprising 0.5 to 25% by weight polyacrylamide, based on the total weight of the hydrogel. The hydrogel, in any of the above-described embodiments, is suitable for the method of the invention.

Upon administration of the hydrogel, a thin layer of connective tissue surrounds the endoprosthesis, enabling the endoprosthesis to become a stable part of the connective tissue. Due to the stability of the hydrogel and the thin layer of connective tissue, the endoprosthesis may be removed from the patient. This advantage is at least in part due to the stability of the hydrogel which in turn is at least in part due to the washing process.

Several factors affect the rheological properties of the hydrogel, such as the relative amount of monomer used. the relative amount of initiator, the temperature and other parameters of the polymerisation process. and the washing process. Thus, the polymerisation process may provide a hydrogel with an array of viscosities. The invention is directed to an endoprosthesis typically for the urethra, the rectum or colon (or canalis analis), or the ureter and may thus be tailored to the requirements of the conduit.

An important object of the invention is to provide a prosthetic device for increasing the resistance of conduits selected from the group consisting of the urethra, the rectum or colon (or canalis analis); and the ureter for the treatment of urinary incontinence, anal incontinence, and vesicouretal reflux, respectively, wherein said device is injectable and comprising the hydrogel as described herein.

The method of the invention preferably includes the administering of the hydrogel by means of injecting the hydrogel into the appropriate conduit. In the treatment of urinary incontinence, the hydrogel is typically injected into the urethra, specifically under the submucosal membrane of the urethra. Injection is via the external surface of the urethra and toward the submucosal membrane.

The present investigators have found that typically 2 to 5 mL of the hydrogel are suitable to provide adequate resistance in the urethra by bulking the urethra. Typically, 3 mL of hydrogel is injected and preferably the 2-5 mL are distributed by depositing the gel at more than one cross-sectional position along a single longitudinal position of the urethra. In a particularly suitable embodiment, 3 or more depots are made along a single longitudinal position of the urethra. The present investigators have found that depots 0.5 cm distally from the neck of the bladder are particularly suitable.

The present investigators have found that submucosal injections at positions 10, 2, and 6 o'clock of the cross-sectional axis of the urethra to be particularly suitable for the treatment of urinary incontinence.

The depots are typically made by means of a syringe or by use of a cytoscope or catheter. Suitably a 21 to 27G needle is employed for the injection.

For the treatment of anal incontinence, the hydrogel is typically injected into the colon or rectum (canalis analis) specifically under the submucosal membrane of the colon or rectum. Injections of 2 to 6 ml are suitable. The hydrogel is preferably distributed at more than one cross-sectional position along a single longitudinal position of the colon or rectum. In a particularly suitable embodiment. 3 or more depots are made along a single longitudinal position of the colon or rectum, preferably at positions 10, 2, and 6 o'clock of the cross-sectional axis of the colon or rectum.

For the treatment of vesicouretal reflux, submucosal injections into the ureter of the patient is required. Injections of 2 to 5 ml are suitable. The hydrogel is preferably distributed at more than one cross-sectional position along a single longitudinal position of the ureter In a particularly suitable embodiment, 3 or more depots are made along a single longitudinal position of the ureter, preferably at positions 10, 2, and 6 o'clock of the cross-sectional axis of the ureter.

In an alternative embodiment of the invention, the method comprises the use of a prosthetic device comprising cells, such as stem cells. Polyacrylamide provides an excellent template and matrix for cell growth. The use of cells in combination with the hydrogel of the invention for the preparation of the device would allow for cellular engraftment to the surrounding tissue in the ureter, urethra or analis canalis. A method comprising the hydrogel of the invention and the appropriate cells allows for greater resistance and greater efficiency in providing resistance.

EXAMPLES

Example 1

Preparation of Hydrogel

The gel is a polyacrylamide gel manufactured by a polymerisation of the monomers of acrylamide and N,N'-methylene-bis-acrylamide. The finished product may have different viscosities.

The hydrogel has the empirical formula $[C_3H_5NO]_x$ $[C_7H_{10}N_2O_2]_y$ and the structural formula as shown below

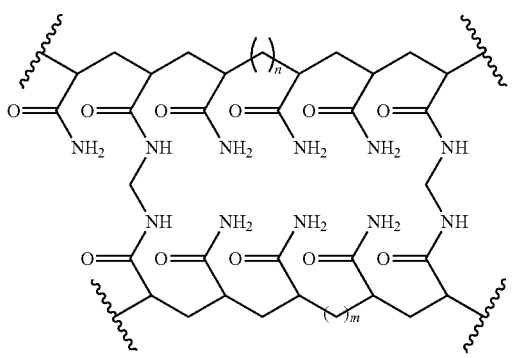

The hydrogel typically contains approximately 95% water. The concentration of the monomers acrylamide and N,N'-methylene-bis-acrylamide has been shown to be less than 10 ppm and is adequate for the desired stability of the final product, often less than 5 ppm.

The finished product must conform with respect to pH, absence of heavy metals, refractive index, stability, absence of pyrogens, and must be sterile, practically inert, and be substantially free of monomers.

Preparation 1.1

The synthetic preparation suitably involves the following operations:

1. Two mixtures, A1 and A2, are prepared. A1 comprises water, acrylamide, N,N'-methylene-bis-acrylamide, N,N,N',N'-tetramethylene-ethylene-diamine (TEMED). A2 comprises water and ammonium persulphate;
2. The two mixtures are combined in the following ratio: 1990 mL of A1 and 10 mL of A2 and kept at 45° C. and degassed with nitrogen for 20 seconds;
3. The reaction mixture is cast into several 100 mL beakers:
4. Polymerisation is allowed to occur for 0.5 to 1.5 hours;
5. The gel is demolded;
6. Residual monomers are extracted and with equilibration in WFI water for 92 hours, changing the water several times, typically 8 times during the 92 hours;
7. The purified gels are homogenised by grinding with an vertically oscillating grid;
8. The syringe is filled with the homogenised gel material;
9. Autoclavation of the syringe A typical method for preparing the hydrogel may be summarised as:

Preparation 1.2

Process summary. The gel is prepared by mixing an aqueous monomer solution of acrylamide (AM) and N,N'-methylene-bis-acrylamide (BISAM) as cross-linker with N,N,N',N'-tetramethylene ethylene diamine (TMED) as co-initiator and ammoniumpersulfate (APS) as free-radical initiator (redox-system). By degassing a bulk solution with nitrogen polymerisation starts. After final polymerisation the gel transferred into a washing tank with net trays onto which the gel is placed. During water washing the gel swells and monomer residues are extracted. The swollen gel is fed and evacuated in a filling unit having the gel delivered in a syringe, which is autoclaved.

Two alternate formulations have been prepared, a lower- and a higher-end viscosity formulation. Both formulations have a solid weight content of less than 3.5% and a complex viscosity module in the range of 2 to 50 Pa s, typically between 3 and 20 Pa s.

TABLE 1

| Chemical constituent | lower end viscosity | higher end viscosity |
|---|---|---|
| acrylamide | 502 g | 547 g |
| N,N'-methylene-bis-acrylamide | 2.2 g | 4.6 g |
| TMED | 3.0 g | 2.6 g |
| APS | 5.4 g | 5.0 g |
| Non-pyrogenic water | Add 10 litre | Add 10 litre |

The above are typical preparations of the hydrogel and may be adjusted within certain ranges.

Preparation 1.3

Polyacrylamide Formulations from Inline Cross-Linking Process

A particularly interesting method of preparing the hydrogels of the invention involves an inline cross-linking process. Two individual and eventually degassed flows, one being a pre-mix of acrylic amide, bis-methylene acryl amide (the cross-linker) and TEMED, the other being the AMPS initiator solution, are pumped into a static mixer for mixing, chemical initiation and subsequent extrusion downstream into a pipe reactor made of Teflon or steel in which the polymerisation occurs. Washing of the gel is simplified due to high surface area of gel from reactor.

By selecting monomer, cross-linker and initiator concentrations and their relative molar ratios, and by regulating the two flow rates and the polymerisation temperatures, it is possible to produce gels that are varying in degree of crosslinking and in solids content.

Preparation 1.4

The reagents were combined in ratios described in Tables 2, 3 and 4, and washed as described in the Tables (with pyrogen-free water unless indicated otherwise) to give low, medium, and high viscosity formulations. Hydrogels with solid weight contents between 0.5 and 25% polyacrylamide were prepared.

TABLE 2

| Process parameters and features of resulting gel: low viscosity formulations | | | | | | | | |
|---|---|---|---|---|---|---|---|---|
|  | lv1 | lv2 | lv3 | lv4 | lv5 | lv6 | lv7[d] | lv8[e] |
| washing time (hrs) | a) | 19.5 | 73.75 | 92 | 94.3 | 72.8 | 93.6 | 93.9 |
| dry matter[f] (%) | 2.55 | 2.08 | 2.63 | 2.87 | 2.89 | 3.15 | 3.68 | 3.17 |
|  |  | 2.36 | 2.58 | 2.67 | 2.82 | 2.90 | 3.57 | 3.52 |
|  |  |  | 2.09 |  |  |  |  |  |
| molar ratio AM:bisAM | b) | 976 | 700 | 488 | 366 | 3239 | 488 | 488 |
| molar ratio AM + BISAM:TEMED | 252 | 252 | 253 | 251 | 252 | 249 | 252 | 252 |

TABLE 2-continued

Process parameters and features of resulting gel: low viscosity formulations

| molar ratio AM + BISAM:APS | 298 | 299 | 298 | 298 | 298 | 299 | 298 | 298 |
|---|---|---|---|---|---|---|---|---|
| residual monomer in ppm | c) | 89 | 5 | 2.97 | 2 | 5 | 1.4 | 0.97 |
| elasticity G' in Pa | 0.16 | 5.23 | 14.3 20.1 | 26.6 | 57.05 | 71.7 | 39.2 | 28.5 |
| viscosity in Pa s | .045 | .88 | 2.35 3.30 | 4.37 | 9.1 | 11.5 | 6.29 | 4.55 |
| gelation time (min) | liquid | highly viscous liquid | 12 | 2 | 2 | 2 | 2.5 | 2.5 |

|  | lv9 | lv10 | lv11 | lv11 | lv12 |
|---|---|---|---|---|---|
| washing time (hrs) | 121 | 96.4 |  |  |  |
| dry matter (%) | 2.18 | (5.10)$^f$ | (10.2)$^f$ | (10.1)$^f$ | (20.2)$^f$ |
| molar ratio AM:bisAM | 701 | 701 | 488 | 488 | 488 |
| molar ratio AM + BISAM:TEMED | 252 | 252 | 252 | 504 | 2016 |
| molar ratio AM + BISAM:APS | 298 | 298 | 298 | 596 | 2385 |
| residual monomer in ppm | 0.97 |  |  |  |  |
| elasticity G' in Pa | 28.5 | 11.1 | (911)$^g$ | (1240)$^g$ | (9460)$^g$ |
| viscosity in Pa s | 4.55 | 1.8 | (145)$^g$ | (197)$^g$ | (1505)$^g$ |
| gelation time (min) |  | 3.17 | 0.00 | 1.21 | 3.5$^h$ | a) material was liquid so washing was a dilution
b) infinite
c) since washing was not an extraction but a dilution, the residual monomer was merely decreased by the dilution factor (508 ppm to 254 ppm).
$^d$casting and washing done using 0.9% NaCl aqueous solution
$^e$casting with water; washing done using 0.9% NaCl aqueous solution
$^f$pre-wash values - washing typically reduces value by 30-55%
$^g$pre-eash values - washing typically reduces value by 20-40%
$^h$highly notch sensitive
$^i$variations in values may be due to measurement performance techniques or to location in the batch from which sample was taken

TABLE 3

Process parameters and features of resulting gel: medium viscosity formulations

|  | mv1 | mv2 | mv3 | mv4 | mv5 |
|---|---|---|---|---|---|
| washing time (hrs) | 97 | 211.5 | 96 | 94.8 | 90.3 |
| dry matter (%) | 3.14 | 2.49 | 3.25 | 3.29 | 3.22 |
| molar ratio AM:bisAM | 310 | 310 | 290 | 289 | 289 |
| molar ratio AM + BISAM:TEMED | 252 | 252 | 252 | 251 | 252 |
| molar ratio AM + BISAM:APS | 299 | 299 | 299 | 299 | 299 |
| residual monomer in ppm | 1.6 |  | 1.5 |  |  |
| elasticity G' in Pa | 108.5 |  | 129 | 133.5 |  |
| viscosity in Pa s | 17.4 |  | 20.6 | 21.30 |  |
| gelation time (min) | 2.5 | 2.5 | 2.18 |  |  |

TABLE 4

Process parameters and features of resulting gel: high viscosity formulations

|  | hv1 | hv2 | hv3 | hv4 | hv5 |
|---|---|---|---|---|---|
| washing time (hrs) | 119.5 | 516 | 122 | 95.5 | 116.7 |
| dry matter (%) | 3.47 | 2.5 | 3.56 | 3.83 | 3.42 |
| molar ratio AM:bisAM | 260 | 260 | 260 | 260 | 260 |
| molar ratio AM + BISAM: TEMED | 315 | 315 | 604 | 313 | 314 |
| molar ratio AM + BISAM: APS | 376 | 376 | 755 | 375 | 376 |
| residual monomer in ppm |  | 0.2 |  |  |  |
| elasticity G' in Pa | 343 | 274 |  | 314.5 |  |
| viscosity in Pa s | 54.7 | 43.65 |  | 50.1 |  |
| gelation time (min) | 2.18 | 2.18 | 7.5 |  |  |

Example 2

Method of Administration and Clinical Results
Treatment by Injection

The polyacrylamide hydrogel (solid weight content 2.5% and ca. 97.5% pyrogen-free water) is injected under the mucous membrane of the urethra so as to provide increased density of the urethra. It is carried out by during short procedure involving few complications.

The medical procedure involves injection of polyacrylamide gel under the mucous membrane of the urethra of women suffering from incontinence. Injection is via the external surface of the urethra and toward the submucosal membrane. 3 mL are injected at three depots sites are made along a single longitudinal position of the urethra. Depots 0.5 cm distally from the neck of the bladder were made.

The injections are carried out under a local anaesthetic, enabling the bladder to be filled subsequently and the patients to cough in order to establish immediately whether sufficient density for urinary incontinence has been achieved. On lack of effect, the injection may be repeated which is common in connection with treatment by injection.

Examination of the woman found the treatment by injection suitable according to the standards and regimes of the Gynaecology-Obstetrics department of Copenhagen's Amstsygehus (County Hospital) in Glostrup. Results and any complications are monitored at check-up examinations every three months for one year after the treatment.

The invention claimed is:

1. A method of treating anal incontinence comprising administering an endoprosthesis, which includes a hydrogel, to a mammal, said hydrogel comprising 0.5 to 25% by weight, based on the total weight of the hydrogel, of a polyacrylamide prepared by a method comprising combining acrylamide and methylene bis-acrylamide; wherein said hydrogel includes less than 50 ppm monomeric units, has a complex viscosity of about 2 to 50 Pas and has an elasticity modulus of about 1 to 200 Pa.

2. A method of treating anal incontinence comprising directly injecting a hydrogel into at least one of the conduits selected from the group consisting of a rectum and a colon, wherein the hydrogel comprises water or aqueous solution and about 0.5 to 25% by weight polyacrylamide having fewer than 50 ppm monomer units and having a complex viscosity of about 2 to 50 Pas and an elasticity modulus of about 1 to 200 Pa, the polyacrylamide prepared by combining acrylamide and methylene bis-acrylamide.

3. The method of claim 2 wherein the aqueous solution is a saline solution.

4. The method according to claim 1 or 2, wherein the polyacrylamide is prepared by combining acrylamide and methylene bis-acrylamide in a molar ratio of 150:1 to 1000:1.

5. The method according to claim 1 or 2, wherein the hydrogel comprises less than 15% by weight of the polyacrylamide, based on the total weight of the hydrogel.

6. The method according to claim 1 or 2, wherein the hydrogel comprises at least 1% by weight of the polyacrylamide, based on the total weight of the hydrogel.

7. The method according to claim 1 or 2, wherein the hydrogel has a complex viscosity module of about 2 to 50 Pas.

8. The method according to claim 1 or 2, wherein the hydrogel comprises at least 80% by weight pyrogen-free water or saline solution.

9. The method according to claim 8, wherein the pyrogen-free or water or saline solution is a saline solution.

10. The method according to claim 8, wherein the pyrogen-free water or saline solution is pyrogen free water.

11. The method according to claim 1, wherein the administering comprises injecting the hydrogel.

12. The method according to claim 11, wherein the injecting of the hydrogel comprises injections at positions 10, 2, and 6 o'clock of the cross-sectional axis of the colon or rectum.

13. The method according to claim 1 or 2, further comprising the inclusion of cells.

14. The method according to claim 13, wherein the cells comprise stem cells.

15. The method according to claim 13, wherein the cells allow for cellular engraftment to the surrounding tissue in the analis canalis.

16. The method according to claim 1 or 2, wherein the hydrogel comprises less than 10% by weight of the polyacrylamide, based on the total weight of the hydrogel.

17. The method according to claim 1 or 2, wherein the hydrogel comprises less than 7.5% by weight of the polyacrylamide, based on the total weight of the hydrogel.

18. The method according to claim 1 or 2, wherein the hydrogel comprises less than 5% by weight of the polyacrylamide, based on the total weight of the hydrogel.

19. The method according to claim 1 or 2, wherein the hydrogel comprises less than 3.5% by weight of the polyacrylamide, based on the total weight of the hydrogel.

20. The method according to claim 1 or 2, wherein the hydrogel comprises at least 1.6% by weight of the polyacrylamide, based on the total weight of the hydrogel.

21. The method according to claim 1 or 2, wherein the hydrogel has a complex viscosity of about 2 to 40 Pas.

22. The method according to claim 1 or 2, wherein the hydrogel has a complex viscosity of about 2 to 30 Pas.

23. The method according to claim 1 or 2, wherein the hydrogel has a complex viscosity of about 2 to 20 Pas.

24. The method according to claim 1 or 2, wherein the hydrogel comprises at least 75% by weight pyrogen-free water or saline solution.

25. The method according to claim 1 or 2, wherein the hydrogel comprises at least 85% by weight pyrogen-free water or saline solution.

26. The method according to claim 1 or 2, wherein the hydrogel comprises at least 90% by weight pyrogen-free water or saline solution.

27. The method according to claim 1 or 2, wherein the hydrogel comprises at least 95% by weight water or aqueous solution.

28. The method according to claim 1 or 2, wherein the polyacrylamide is substantially comprised of cross-linked polyacrylamide.

29. The method according to claim 1 or 2, wherein the polyacrylamide consists essentially of a polyacrylamide crosslinked with methylene bis-acrylamide.

30. The method according to claim 1 or 2, wherein the hydrogel has an elasticity modulus of about 5 to 150 Pa.

31. The method according to claim 1 or 2, wherein the hydrogel has an elasticity modulus of about 10 to 100 Pa.

32. The method according to claim 1 or 2, wherein the elasticity modulus and the complex viscosity are related by a factor of 5.8 to 6.4.

* * * * *